(12) United States Patent
Grashow (10) Patent No.: US 10,792,458 B2
(45) Date of Patent: Oct. 6, 2020

(54) RAINOUT CONTROL IN A PRESSURE SUPPORT SYSTEM

(71) Applicant: KONINKLIJKE PHILIPS N.V., Eindhoven (NL)

(72) Inventor: Jonathan Sayer Grashow, Cheswick, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1121 days.

(21) Appl. No.: 15/168,958

(22) Filed: May 31, 2016

(65) Prior Publication Data

US 2016/0354567 A1 Dec. 8, 2016

Related U.S. Application Data

(60) Provisional application No. 62/170,301, filed on Jun. 3, 2015.

(51) Int. Cl.
*A61M 16/16* (2006.01)
*A61M 16/00* (2006.01)
(Continued)

(52) U.S. Cl.
CPC ........ *A61M 16/161* (2014.02); *A61M 16/024* (2017.08); *A61M 16/0683* (2013.01);
(Continued)

(58) Field of Classification Search
CPC ... A62B 9/003; A61M 16/0003; A61M 16/10; A61M 16/1075–1095; A61M 16/161; A61M 2205/36–3606
See application file for complete search history.

(56) References Cited

U.S. PATENT DOCUMENTS 5,148,802 A 9/1992 Sanders
5,313,937 A 5/1994 Zdrojkowski
(Continued)

OTHER PUBLICATIONS

Doheny K., "Sleep Disorders Health Center Can't Sleep? Adjust the Temperature", 2005-2016 Webmed LLC (Reference: http://www.webmd.com/sleep-disorders/features/cant-sleep-adjust-the-temperature.
(Continued)

*Primary Examiner* — Timothy A Stanis
*Assistant Examiner* — Charles M Vivian
(74) *Attorney, Agent, or Firm* — Michael W. Haas (57) ABSTRACT

A pressure support system includes a pressure generating device, an airflow path, and a control system. The control system is structured to determine a first measurement indicative of an amount of water vapor in the airflow path or an amount of condensation in the airflow path and generate a number of control signals structured to control an environmental control device structured to control an environmental parameter in an environment including the pressure support system, wherein the control signals are generated based on at least the first measurement and are configured to cause the environmental control device to adjust the environmental parameter in a manner that will reduce a degree or a likelihood of rainout in the airflow path, and transmit the control signals to the environmental control device so that it may be controlled to reduce the degree or likelihood of rainout.

17 Claims, 5 Drawing Sheets

(51) Int. Cl.
*A61M 16/06* (2006.01)
*F24F 11/30* (2018.01)
*F24F 110/20* (2018.01)

(52) U.S. Cl.
CPC ............... *A61M 2205/3368* (2013.01); *A61M 2205/3561* (2013.01); *A61M 2205/3584* (2013.01); *A61M 2205/3592* (2013.01); *A61M 2205/502* (2013.01); *F24F 11/30* (2018.01); *F24F 2110/20* (2018.01)

(56) References Cited

U.S. PATENT DOCUMENTS

| | | | |
|---|---|---|---|
| 5,433,193 | A | 7/1995 | Sanders |
| 5,632,269 | A | 5/1997 | Zdrojkowski |
| 5,803,065 | A | 9/1998 | Zdrojkowski |
| 6,029,664 | A | 2/2000 | Zdrojkowski |
| 6,539,940 | B2 | 4/2003 | Zdrojkowski |
| 6,626,175 | B2 | 9/2003 | Jafari |
| 7,011,091 | B2 | 3/2006 | Hill |
| 2005/0143617 | A1 | 6/2005 | Auphan |
| 2006/0037613 | A1* | 2/2006 | Kwok .................. A61M 16/16 128/203.27 |
| 2007/0169776 | A1 | 7/2007 | Kepler |
| 2009/0223514 | A1* | 9/2009 | Smith ................ A61M 16/1075 128/203.14 |
| 2011/0010014 | A1 | 1/2011 | Oexman |
| 2011/0120462 | A1* | 5/2011 | Tatkov .............. A61M 16/1075 128/203.14 |
| 2012/0125334 | A1* | 5/2012 | Korneff ................ A61M 11/005 128/203.26 |
| 2013/0160766 | A1* | 6/2013 | Malouf ............. A61M 16/0808 128/203.12 |
| 2013/0324788 | A1 | 12/2013 | Holley |
| 2014/0081654 | A1 | 3/2014 | Bechtel |
| 2014/0116440 | A1 | 5/2014 | Thompson |
| 2015/0027204 | A1* | 1/2015 | Stoks .................. A61M 16/024 73/31.05 |
| 2015/0320588 | A1* | 11/2015 | Connor ................ A61F 7/0097 607/107 |

OTHER PUBLICATIONS

Smarthome—Home Automation Systems, Products, Kits, Hubs & Ideas, Copyright 1995-2016 Smarthome http://www.smarthome.com/29937/Ecobee-EB-EMSSI-01-Wi-Fi-Commercial-Programmable-Thermostat/p.aspx.

* cited by examiner

RAINOUT CONTROL IN A PRESSURE SUPPORT SYSTEM

CROSS-REFERENCE TO RELATED APPLICATIONS

This patent application claims the priority benefit under 35 U.S.C. § 119(e) of U.S. Provisional Application No. 62/170,301, filed on Jun. 3, 2015, the contents of which are herein incorporated by reference.

BACKGROUND OF THE INVENTION

1. Field of the Invention

The present invention pertains to airway pressure support devices, and, in particular, to a system and method for monitoring and controlling the degree of rainout in a pressure support device by automatically controlling a parameter affecting rainout, such as one or more environmental conditions.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory airflow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory airflow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

"Rainout" is a condition that occurs when the humidity of the air within the air flow path of a pressure support system (e.g. the CPAP unit, hose, and mask) condenses on the inside surfaces of the components of the air flow path, resulting in pooling of water within the airflow path over time (which is a nuisance to the patient receiving therapy). When rainout occurs, it often disturbs the patient, which in turn may cause the patient to discontinue therapy for the remainder of the night. Rainout occurs because the air within the airflow path is heated and humidified by the pressure support device (or the patient's own body in the case of exhaled air), but the temperatures of the walls of the airflow circuit (e.g. a hose or mask) are equilibrated with the ambient environment which may be significantly cooler than the air in the airflow circuit. The temperature of the air within the airflow circuit decreases when it makes contact with the walls of the circuit, resulting in condensation (i.e. "rainout"). Some pressure support systems attempt to reduce rainout by adding heating elements to the walls of the airflow circuit (e.g. a heated hose), but this is only a partial solution since it is impractical to add heating elements to all of the surfaces of the airflow circuit. Also, the addition of heating elements and associated electronics is expensive and adds additional weight to the system (especially important for wearable components).

SUMMARY OF THE INVENTION

Accordingly, it is an object of the present invention to provide a pressure support device that overcomes the shortcomings of conventional pressure support devices. This object is achieved according to one embodiment of the present invention by providing a pressure support system for delivering a flow of breathing gas to an airway of a patient that includes a pressure generating device structured to generate the flow of breathing gas, an airflow path coupled to the pressure generating device and structured to carry the flow of breathing gas, and a control system, wherein the control system stores and is structured to execute a number of routines. The routines are structured to determine a first measurement indicative of an amount of water vapor in the airflow path or an amount of condensation in the airflow path and generate a number of control signals structured to control an environmental control device structured to control an environmental parameter in an environment including the pressure support system, wherein the control signals are generated based on at least the first measurement and are configured to cause the environmental control device to adjust the environmental parameter in a manner that will reduce a degree or a likelihood of rainout in the airflow path. The routines are further structured to transmit the control signals to the environmental control device so that it may be controlled to reduce the degree or likelihood of rainout.

It is yet another object of the present invention to provide a method of controlling rainout in a pressure support device that does not suffer from the disadvantages associated with conventional rainout control techniques. This object is achieved by providing a method of controlling rainout in a pressure support system for delivering a flow of breathing gas to an airway of a patient through an airflow path that includes determining a first measurement indicative of an amount of water vapor in the airflow path or an amount of condensation in the airflow path, generating a number of control signals structured to control an environmental control device structured to control an environmental parameter in an environment including the pressure support system, wherein the control signals are generated based on at least the first measurement and are configured to cause the environmental control device to adjust the environmental parameter in a manner that will reduce a degree or a likelihood of rainout in the airflow path, and transmitting the control signals to the environmental control device.

In still another embodiment, a method of controlling rainout in a pressure support system for delivering a flow of breathing gas to an airway of a patient through in airflow path including a patient circuit having an exhaust vent for exhausting exhaled gas from the patient circuit is provided. The method includes determining a first measurement indicative of an amount of water vapor in the airflow path or an amount of condensation in the airflow path, and controlling a ratio of the breathing gas to the exhaled gas within the airflow path based on at least the first measurement.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

As used herein, the term "dew point" shall mean the temperature at which the water vapor in a sample of air at constant barometric pressure condenses into liquid water at the same rate at which it evaporates.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
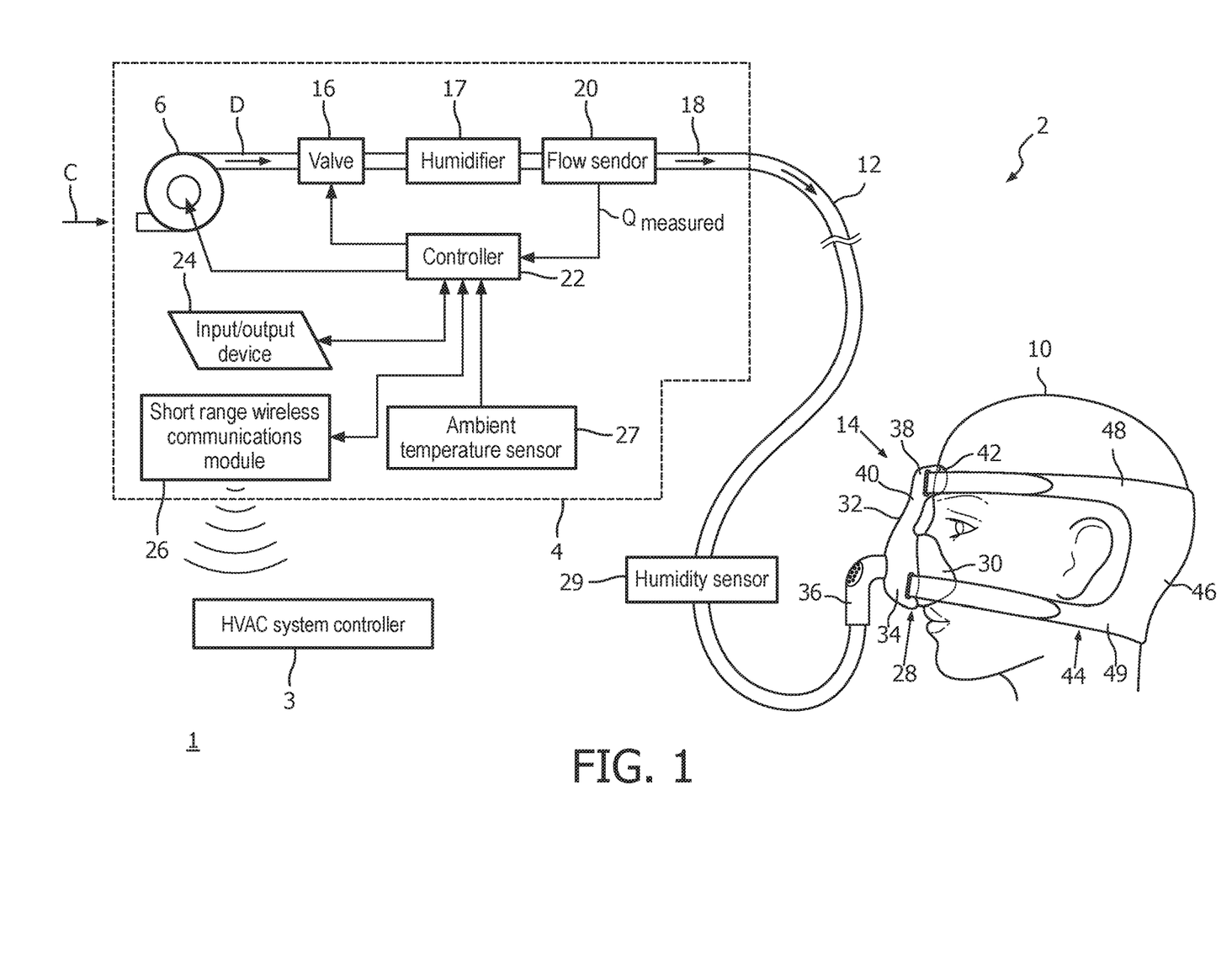
FIG. 1 is a schematic diagram showing an airway pressure support system according to an exemplary embodiment which is operated within an environment, such as a bedroom or home of the user of airway pressure support system.

FIG. 1 is a schematic diagram showing an airway pressure support system 2 according to one particular, non-limiting exemplary embodiment which is operated within an environment 1, such as a bedroom or home of the user of airway pressure support system 2. As seen in FIG. 1, environment 1 includes an environmental control system, such as the exemplary heating, ventilation and air conditioning (HVAC) system controller 3, that is structured to enable selective control of one or more environmental conditions within environment 1, such as, without limitation, temperature or humidity. As described in detail herein, pressure support system 2 is provided with functionality that enables it to monitor a parameter relating to rainout within pressure support system 2 and, in response thereto, control one or more environmental conditions by sending a number of control signals to the environmental control system such as HVAC system controller 3.

Referring to FIG. 1, airway pressure support system 2 includes a pressure generating device base unit 4 which houses a gas flow generator 6, such as a blower used in a conventional CPAP or bi-level pressure support device. Gas flow generator 6 receives breathing gas, generally indicated by arrow C, from the ambient atmosphere and generates a flow of breathing gas therefrom for delivery to an airway of a patient 10 at relatively higher and lower pressures, i.e., generally equal to or above ambient atmospheric pressure. In the exemplary embodiment, gas flow generator 6 is capable of providing a flow of breathing gas ranging in pressure from 3-30 cmH2O. The pressurized flow of breathing gas from gas flow generator 6, generally indicated by arrow D, is delivered via a delivery conduit 12 to a patient interface device 14 of any known construction, which is typically worn by or otherwise attached to patient 10 to communicate the flow of breathing gas to the airway of patient 10. Delivery conduit 12 and patient interface device 14 are typically collectively referred to as a patient circuit.

Pressure support system 2 shown in FIG. 1 is what is known as a single-limb system, meaning that the patient circuit includes only delivery conduit 12 connecting patient 10 to pressure support system 2. As such, an exhaust vent is provided in patient interface device 14 for venting exhaled gases from the system. It should be noted that the exhaust vent can be provided at other locations in addition to or instead of in patient interface device 14, such as in delivery conduit 12. It should also be understood that the exhaust vent can have a wide variety of configurations depending on the desired manner in which gas is to be vented from pressure support system 2.

The present invention also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

In the illustrated embodiment, pressure support system 2 includes a pressure controller in the form of a valve 16 provided in an internal delivery conduit 18 provided in pressure generating device base unit 4 of pressure support system 2. Valve 16 controls the pressure of the flow of breathing gas from gas flow generator 6 that is delivered to patient 10. For present purposes, gas flow generator 6 and valve 16 are collectively referred to as a pressure generating system because they act in concert to control the pressure and/or flow of gas delivered to patient 10. However, it should be apparent that other techniques for controlling the pressure of the gas delivered to patient 10, such as varying the blower speed of gas flow generator 6, either alone or in combination with a pressure control valve, are contemplated by the present invention. Thus, valve 16 is optional depending on the technique used to control the pressure of the flow of breathing gas delivered to patient 10. If valve 16 is eliminated, the pressure generating system corresponds to gas flow generator 6 alone, and the pressure of gas in the patient circuit is controlled, for example, by controlling the motor speed of gas flow generator 6.

Pressure support system 2 further includes a flow sensor 20 that measures the flow of the breathing gas within delivery conduit 18 and delivery conduit 12. In the particular embodiment shown in FIG. 1, flow sensor 20 is interposed in line with delivery conduits 18 and 12, most preferably downstream of valve 16. Flow sensor 20 generates a flow signal, $Q_{MEASURED}$, that is provided to a controller 22 and is used by controller 22 to determine the flow of gas at patient 10 ($Q_{PATIENT}$).

Techniques for calculating $Q_{PATIENT}$ based on $Q_{MEASURED}$ are well known, and take into consideration the pressure drop of the patient circuit, known leaks from the system, i.e., the intentional exhausting of gas from the circuit as described herein, and unknown (unintentional) leaks from the system, such as leaks at the mask/patient interface. The present invention contemplates using any known or hereafter developed technique for calculating total leak flow $Q_{LEAK}$, and using this determination in calculating $Q_{PATIENT}$ based on $Q_{MEASURED}$ (and for other purposes as described elsewhere herein). Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 10 are contemplated by the present invention, such as, without limitation, measuring the flow directly at patient 10 or at other locations along delivery conduit 12, measuring patient flow based on the operation of gas flow generator 6, and measuring patient flow using a flow sensor upstream of valve 16.

Controller 22 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 2, including monitoring a parameter relating to rainout within the air flow path (i.e., internal conduit 18 and the patient circuit comprising livery conduit 12 and patient interface device 14) of pressure support system 2 and, in response thereto, control one or more environmental conditions of environment 1 to reduce the likelihood or degree of rainout as described in greater detail herein.

An input/output device 24 is provided for setting various parameters used by airway pressure support system 2, as well as for displaying and outputting information and data to a user, such as a clinician or caregiver.

As seen in FIG. 1, pressure generating device base unit 4 in the exemplary embodiment also includes a short range wireless communications module 26 which is operatively coupled to controller 22. In the exemplary embodiment, short range wireless communications module 26 is a module that is structured and configured to enable pressure generating device base unit 4 to communicate with other, similarly equipped electronic devices (e.g., HVAC system controller 3 as described herein) over a short range wireless network. In the exemplary embodiment, short range wireless communications module 26 is a Bluetooth® module that is structured and configured to enable pressure generating device base unit 4 to communicate with other devices over an ad hoc Bluetooth® network. It will be appreciated, however, that other communication techniques/protocols, such as, without limitation, Wi-Fi, infrared light, near field communication (NFC), other RF based systems, or a wired connection, etc., may also be used within the scope of the present invention. In addition, short range wireless communications module 26 may be incorporated within pressure generating device base unit 4, or may be a module that is selectively connectable to pressure generating device base unit 4 via a USB port or other suitable connection.

Furthermore, in the illustrated embodiment, pressure support system 2 also includes a humidifier 17 provided in the main housing of pressure support system 2. Alternatively, humidifier 17 may be separate from and located external to the main housing. Humidifier 17 is controlled by controller 22. Humidifier 17 further improves comfort by providing moisture in the supplied gas. In the exemplary embodiment, humidifier 17 is a passover type humidifier. U.S. Patent Application Publication No. 2007/0169776, incorporated herein by reference in its entirety, discloses an exemplary humidifier device suitable for use in the present invention. Humidifier devices having alternative designs, such as a non-passover type humidifier that employs nebulization, atomization, vaporization or a combination thereof, may also be used.

As seen in FIG. 1, pressure support system 2 also includes an ambient temperature sensor 27 that is operatively coupled to controller 22. In the exemplary embodiment, ambient temperature sensor 27 is supported by the housing of pressure generating device base unit 4, and may be any type of known or hereafter developed sensor device suitable for measuring the temperature of environment 1, such as, without limitation, a thermistor or a thermocouple. Pressure support system 2 further includes a humidity sensor 29 that is provided in the airflow path of pressure support system 2. In the exemplary embodiment, humidity sensor is shown as being provided in delivery conduit 12, although it will be understood that this is meant to be exemplary only and that humidity sensor 29 may be positioned in other portions of the airflow path such as within internal conduit 18 or within patient interface device 14. Humidity sensor 29 may be any type of known or hereafter developed sensor device suitable for measuring the humidity level within the airflow path of pressure support system 2, such as, without limitation, a capacitive humidity sensor, a resistive humidity sensor, or a thermal conductivity humidity sensor. Humidity sensor 29 is coupled to controller 22 by a suitable wired and/or wireless connection to enable the measurements generated by humidity sensor 29 to be communicated to controller 22.

In the exemplary embodiment, patient interface device 14 includes a patient sealing assembly 28, which in the illustrated embodiment is a nasal mask. However, other types of patient sealing assemblies, such as, without limitation, a nasal/oral mask, a nasal cushion, or a full face mask, which facilitate the delivery of the flow of breathing gas to the airway of a patient may be substituted for patient sealing assembly 28 while remaining within the scope of the present invention. Patient sealing assembly 28 includes a cushion 30 coupled to a frame member 32. In the illustrated embodiment, cushion 30 is defined from a unitary piece of soft, flexible, cushiony, elastomeric material, such as, without limitation, silicone, an appropriately soft thermoplastic elastomer, a closed cell foam, or any combination of such materials. Also in the illustrated embodiment, frame member 32 is made of a rigid or semi-rigid material, such as, without limitation, an injection molded thermoplastic or silicone, and includes a faceplate portion 34 to which cushion 30 is fluidly attached. A fluid coupling conduit 36 having an exhaust vent is coupled to an opening in faceplate portion 34 to allow the flow of breathing gas from pressure generating device base unit 4 to be communicated to an interior space defined by cushion 30, and then to the airway of a patient.

Frame member 32 also includes a forehead support member 38 that is coupled to the faceplate portion 34 by a connecting member 40. A forehead cushion 42 is coupled to the rear of forehead support 38 20. In the exemplary embodiment, forehead cushion 42 is made of a material that is similar to the material of cushion 30.

Patient interface device 14 also includes a headgear component 44 for securing patient interface device 14 to the head of patient 10. Headgear component 44 includes a back member 46, upper strap members 48 and lower strap members 49. In the exemplary embodiment, upper strap members 48 and lower strap members 49 each include a hook and loop fastening system, such as VELCRO®, provided on the end thereof to allow headgear component 44 to be secured in a known manner. It will be understood that the described hook and loop fastening arrangement is meant to be exemplary only, and that other selectively adjustable fastening arrangements are also possible within the scope of the present invention.

In the illustrated, non-limiting exemplary embodiment of the present invention, airway pressure support system 2 essentially functions as a CPAP pressure support system, and, therefore, includes all of the capabilities necessary in such systems in order to provide appropriate CPAP pressure levels to patient 10. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 2:
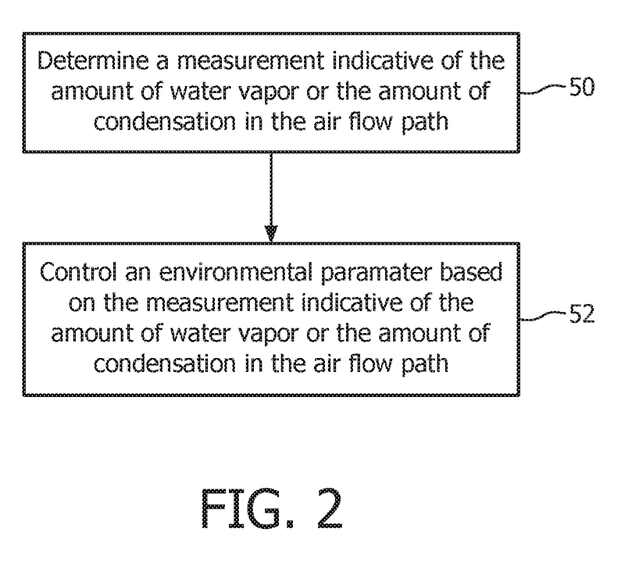
FIG. 2 is a flowchart showing a method for monitoring and controlling rainout according to an exemplary embodiment of the disclosed concept.

FIG. 2 is a flowchart showing a method that may be implemented in pressure support system 2 for monitoring and controlling rainout according to an exemplary embodiment of the disclosed concept. As seen in FIG. 2, the method at its most basic level is a two-step process that includes a first step 50 followed by a second step 52. In the first step 50, pressure support system 2 determines a measurement indicative of the amount of water vapor or the amount of condensation in the airflow path of pressure support system 2. That measurement may take any of a number of different forms, several examples of which are described in greater detail herein. Following step 50, at step 52, pressure support system 2 then takes steps to automatically control an environmental parameter of environment 1 based on the measurement made at step 50. The environmental parameter is controlled in step 52 in a manner which will reduce the degree of and/or eliminate rainout within pressure support system 2. Step 52 may be carried out in any of a number of different ways, several examples of which are described in greater detail herein.

Figure 3:
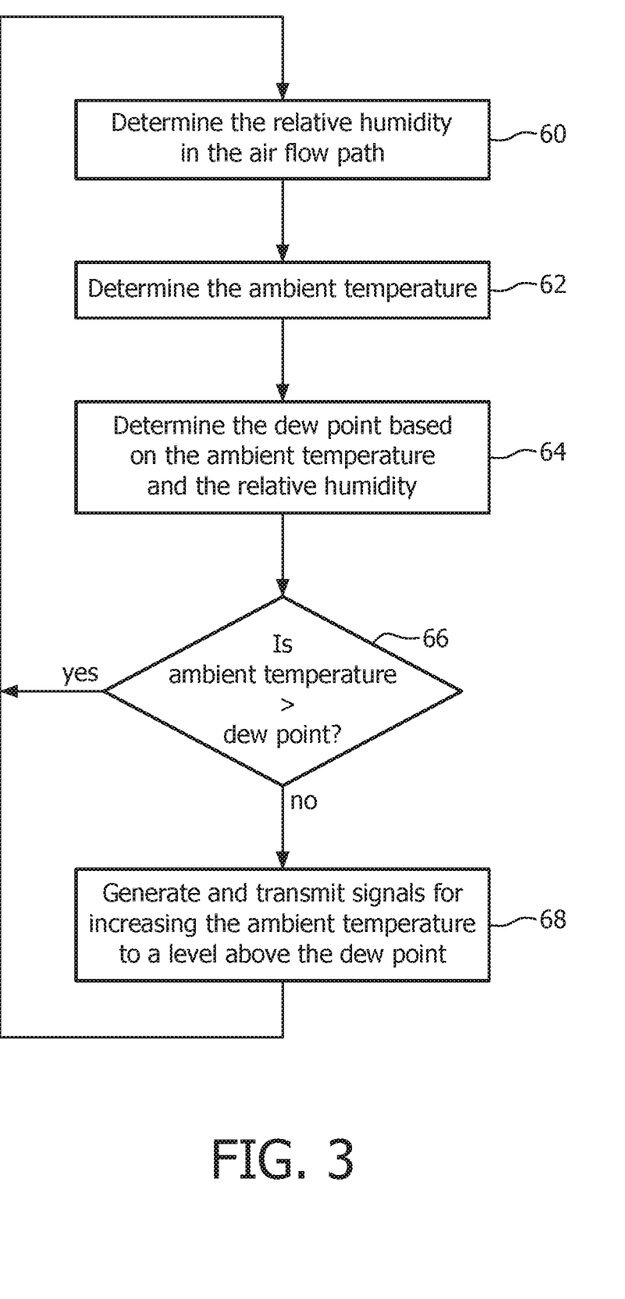
FIG. 3 is a flowchart showing a particular exemplary implementation of the method of FIG. 2.

FIG. 3 is a flowchart showing a particular exemplary implementation of the method just described that may be employed in pressure support system 2 for monitoring and controlling rainout therein. In the exemplary embodiment, the method is implemented in a number of routines stored in the memory of controller 22 and executable by the processor of controller 22. The method of FIG. 3 begins at step 60, wherein the controller 22 determines the relative humidity in the airflow path of pressure support system 2 based on the information received from humidity sensor 29. Next, at step 62, controller 22 determines the ambient temperature of environment 1 based upon the information received from ambient temperature sensor 27. Then, at step 64, controller 22 determines the dew point within the airflow path of pressure support system 2 based on the determined ambient temperature and relative humidity. This dew point determination may be made using any of a number of known or hereafter developed techniques, including, without limitation, a formula or set of formulas, such as the well-known Magnus formula, or using a predetermined lookup table.

The method then proceeds to step 66, wherein a determination is made as to whether the determined ambient temperature is greater than the determined dew point. If the answer at step 66 is yes, then that means that the ambient temperature is not conducive for rainout (a desirable condition) and the method returns to step 60 to continue the monitoring process. If, however, the answer at step 66 is no, then that means that the current ambient temperature is conducive to rainout (not a desirable condition) and should therefore be adjusted so as to minimize and/or eliminate the likelihood of rainout. Thus, if the answer at step 66 is no, the method proceeds to step 68, wherein controller 22 generates a number of control signals that are structured to control HVAC system controller 3 in order to adjust the ambient temperature to a level that is above the dew point determined at step 64. Once generated, those control signals are transmitted wirelessly by short range wireless communications module 26 to HVAC system controller 3, which is structured to receive those control signals and be controlled based thereon. As a result, the ambient temperature in an environment 1 will be increased to a level that is above the determined dew point so as to minimize the likelihood that rainout will occur.

One complicating factor that may be considered in the exemplary embodiment above is the fact that the ambient temperature will not necessarily be the same as the temperature on the inside surfaces of the components making up the airflow path due to the inherent insulating properties of those components. As a result, it may be the case that the airflow path is insulated somewhat from the ambient temperature. Thus, in one particular embodiment, the method may account for this complicating factor by adding and empirically-derived correction factor to the temperature that is used to trigger adjustment in step 66. For example, the method may instead require that the ambient temperature be 10% lower than the dew point before steps are taken to increase the ambient temperature. It will be appreciated that this correction factor could be different for different types of airflow circuits (different hoses, masks, etc.) based on how well each component insulates the airflow circuit from the ambient temperature.

Furthermore, it will be understood that the particular embodiment just described is meant to be exemplary only, and that a number of variations thereof are contemplated within the scope of the disclosed concept. A number of those variations (i.e. alternative embodiments) will now be described.

First, in the method of FIG. 3, rather than relative humidity being measured by humidity sensor 29, at parameter or a similar humidity measurement may instead be estimated based on the settings/parameters of humidifier 17 (e.g., air temperature, heating plate temperature, amount of water in humidifier 17, etc.). One complicating factor is that the human body also humidifies air, so the estimate based on the humidifier parameters as just described could also factor in measured breathing parameters of the patient (title volume, breath rate, minute ventilation, etc.). This alternative may be executed as an empirically driven equation or a lookup table.

In addition, with reference to FIG. 2, the measurement that is determined in step 50 may be an amount of condensation that is present in the airflow path. Thus, in another alternative exemplary embodiment, once that level of condensation is determined, and empirically driven equation or lookup table may then be used to relate that condensation level measurement to an environmental parameter, such as temperature, that is to be controlled as described herein. Condensation level may be determined in a number of different ways. For example, the level of condensation may be detected with a water contact sensor such as, for example, the Sensaphone® spot water detector commercially available from Sensaphone of Aston Pa. As another example, the change of the sound of airflow through the airflow circuit and/or exhalation port as a result of rainout could be sensed using a microphone and converted to a condensation level using an empirically driven equation or lookup table. In still another example, the change in exhalation leak resulting from rainout clogging the exhalation exhaust port could be monitored and converted to a condensation level using an empirically driven equation or lookup table. Condensation level could also be detected based upon patient feedback, such as the patient entering a relative rainout level (e.g., low, medium, high) using input/output device 24. As still another example, a material may be provided within the airflow path that is structured to expand or otherwise change shape when it gets wet. That material could be coupled to a strain gauge or similar sensor which monitors changes in the size and/or shape of the material. The output of the strain gauge or similar sensor may then used to determine a condensation level using an empirically driven equation or a lookup table.

As a further alternative, rather than using temperature sensor 27 to determine ambient temperature, controller 22 may obtain that information from another source, such as through wireless communications from HVAC system controller 3. Once obtained in this manner, that ambient temperature would be used to determine the dew point as described in connection with step 64 of FIG. 3. Ambient temperature information may also be obtained by controller 22 from an external source such as by being downloaded through the Internet.

Figure 4:
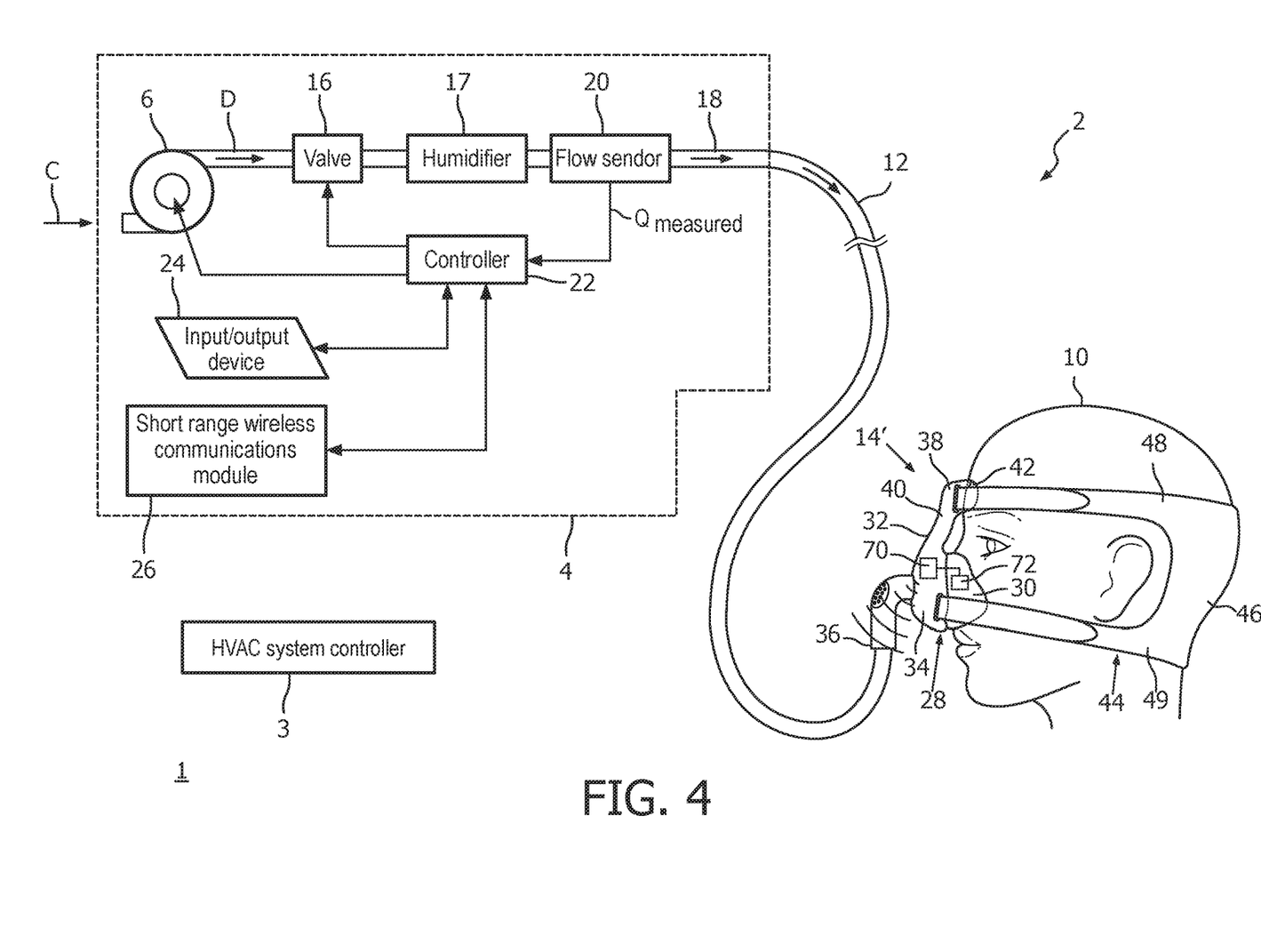
FIG. 4 is a schematic diagram showing an airway pressure support system according to an alternative exemplary embodiment.

FIG. 4 is a schematic diagram showing an airway pressure support system 2' according to an alternative exemplary embodiment which is operated within environment 1. Pressure support system 2' includes many of the same components as pressure support system 2, and like components are labeled with like reference numerals. However, in this embodiment, the monitoring of rainout and adjustment of environmental parameters is performed at alternative patient interface device 14' as described below.

In particular, patient interface device 14' in the exemplary embodiment includes a rainout monitor 70 that is coupled to frame member 32 and a humidity sensor 72 that is provided within a cushion 30 and is coupled to rainout monitor 70. Humidity sensor 72 is similar in structure and functionality to humidity sensor 29 described herein. Rainout monitor 70 and humidity sensor 72 are structured to together implement any of the various embodiments for monitoring and controlling rainout that are described herein.

Figure 5:
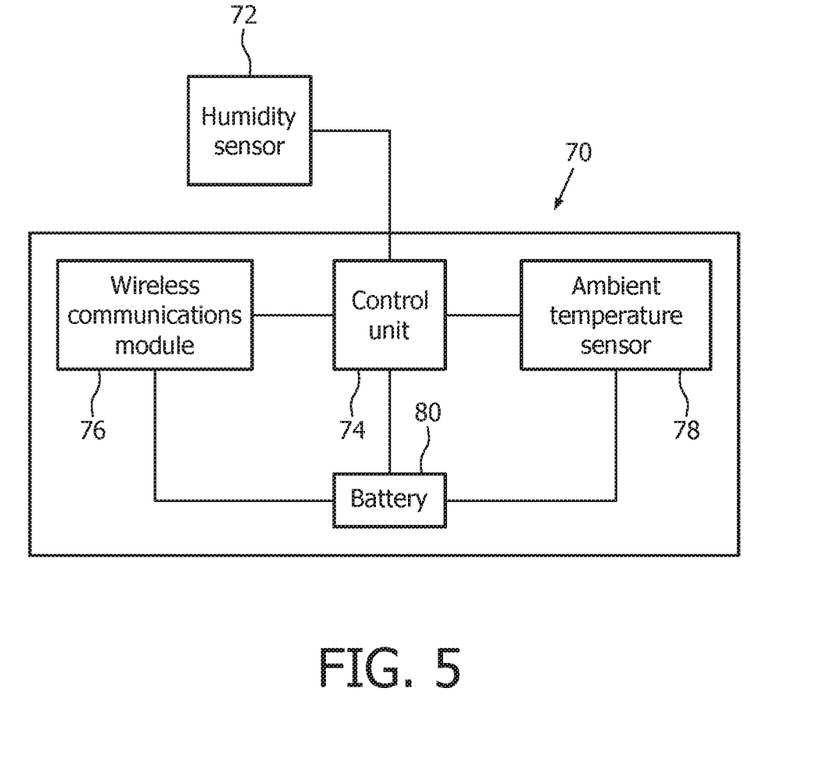
FIG. 5 is a schematic diagram showing a rainout monitor forming a part of the system of FIG. 4.

FIG. 5 is a block diagram of rainout monitor 70 according to the exemplary embodiment. As seen in FIG. 5, rainout monitor 70 is a small electronic device that includes a control unit 74 that is operatively coupled (e.g. by wired or wireless connection) to humidity sensor 72. Control unit 74 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 2 as described herein. Rainout monitor 70 also includes a wireless communications module 76 that is structured to enable wireless communication with HVAC system controller 3.

In the exemplary embodiment, wireless communications module 76 is a Bluetooth® module, although other types of wireless communication modules as described herein may also be used. Rainout monitor 70 further includes an ambient temperature sensor 78 that is similar in structure and functionality to ambient temperature sensor 27 described herein. Finally, in the exemplary embodiment, rainout monitor 70 includes a battery 80 for providing power to the components of rainout monitor 70. It will be understood, however, that this is meant to be exemplary only, and that power may come from other sources, such as, without limitation, a solar cell, power generated from the leak of therapy air from patient interface device 14, power delivered from pressure generating device base unit 4 via a direct wired connection, or power delivered wirelessly via any suitable form of wireless charging (e.g., near field inductive coupling).

As noted above, in this embodiment, control unit 74 is programmed to perform any of the various methods described herein for monitoring rainout and controlling an environmental parameter such as temperature. In particular, in the illustrated embodiment, control unit 74 is programmed to implement the method of FIG. 3 with the relative humidity measurements being made by humidity sensor 72, the ambient temperature measurements being made by ambient temperature sensor 78, and the dew point and temperature control signal generation and transmission being performed by control unit 74 and wireless communications module 76.

Moreover, the air in the airflow circuit of a pressure support system is a mix of fresh air from the air flow generator/humidifier and ex-exhaled air from the patient exhaled air typically has a higher humidity than the air from the air flow generator/humidifier because the human body is a very good humidifier and the body temperature is usually higher than the ambient temperature. Thus, according to a further aspect of the disclosed concept, an alternative approach to reduce rainout would be to automatically increase the ratio of fresh air (from the air flow generator/humidifier) to exhaled air in the airflow circuit. In one particular embodiment, this approach may be implemented by making the exhaust vent of fluid coupling conduit 36 automatically and selectively adjustable such that the amount of air leak from the exhaust vent can be adjusted. This may be accomplished by providing fluid coupling conduit 36 with an adjustable valve or orifice that may be controlled based upon signals from controller 22 or control unit 74 depending upon the implementation to increase or decrease the leak rate as desired. Alternatively, if fluid coupling conduit 36 has a passive exhaust vent, then the pressure generating device 6 could increase the air pressure inside the patient circuit to drive more air through the exhaust port in order to increase the ratio of fresh air to exhaled air in the airflow circuit.

Is still a further alternative, as described elsewhere herein, the amount of thermal isolation between the airflow circuit in the ambient air will factor into the amount of rainout that occurs. Thus, according to yet another aspect of the disclosed concept, controller 22 or control unit 74 could monitor the temperature inside the airflow circuit using a suitable sensor and determine when it would be advantageous to provide additional thermal insulation for the airflow circuit. In one embodiment, when such a determination is made, a signal could be provided through input/output device 24 instructing the patient to put a wrap or some kind of other insulation around a component such as delivery conduit 12 in order to reduce rainout.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system for delivering a flow of breathing gas to an airway of a patient, comprising:
   a pressure generating device structured to generate the flow of breathing gas and provide the flow of breathing gas at an output of the pressure generating device;
   an airflow path coupled to the output of the pressure generating device and structured to receive and carry the flow of breathing gas generated by the pressure generating device;
   a humidity sensor provided in the airflow path, the humidity sensor being structured to generate a first sensed signal comprising a direct measurement of humidity within the airflow path; and
   a control system, wherein the control system stores and is structured to execute a number of routines, the number of routines being structured to:
   determine based on an output of the sensor a first measurement indicative of an amount of water vapor in the airflow path or an amount of condensation in the airflow path,
   generate a number of control signals structured to control an environmental control device structured to control an environmental parameter in an environment outside of the pressure support system, wherein the number of control signals are generated based on at least the first measurement first sensed signal and are configured to cause the environmental control device to adjust the environmental parameter in a manner that will reduce a degree or a likelihood of rainout in the airflow path; and
   transmit the number of control signals to the environmental control device.

2. The pressure support system according to claim 1, wherein the first measurement is a measurement of humidity within the airflow path, and wherein the environmental parameter is ambient temperature within the environment.

3. The pressure support system according to claim 2, wherein the sensor is a humidity sensor structured to generate a first sensed signal indicative of the humidity within the airflow path further including and an ambient temperature sensor structured to generate a second sensed signal indicative of the ambient temperature within the environment, wherein the first measurement is a humidity measurement based on the first sensed signal, wherein the routines are structured to determine a second measurement indicative of the ambient temperature within the environment based on the second sense signal, and wherein the number of control signals is determined based on the first measurement and the second measurement sensed signal and the second sensed signal.

4. The pressure support system according to claim 3, wherein the environmental control device is structured to control the ambient temperature within the environment, and wherein the number of control signals specifies a specific temperature and is structured to control the environmental control device to cause the ambient temperature to equal the specific temperature.

5. The pressure support system according to claim 4, wherein the routines are structured to determine a dew point based on the first measurement sensed signal and the second measurement sensed signal, and wherein the specific temperature is based on the dew point.

6. The pressure support system according to claim 5, wherein the specific temperature is greater than or equal to the dew point.

7. The pressure support system according to claim 5, wherein the specific temperature is offset from the dew point by a predetermined amount.

8. The pressure support system according to claim 1, wherein the pressure generating device and the control system are provided within a pressure generating device base unit, wherein the pressure generating device base unit further includes a wireless communications module coupled to the controller and structured to wirelessly transmit the number of control signals to the environmental control device.

9. The pressure support system according to claim 1, further comprising a patient interface device forming a part of the airflow path, wherein the patient interface device has a rainout monitor attached thereto, wherein the control system is a control unit provided as part of the rainout monitor, and wherein the rainout monitor has a wireless communications module coupled to the control unit and structured to wirelessly transmit the number of control signals to the environmental control device.

10. The pressure support system according to claim 9, wherein the rainout monitor includes an ambient temperature sensor and a the humidity sensor.

11. A method of controlling rainout in a pressure support system for delivering a flow of breathing gas to an airway of a patient through an airflow path, wherein the pressure support system includes a pressure generating device structured to generate the flow of breathing gas and provide the flow of breathing gas at an output of the pressure generating device, and wherein the airflow path is coupled to the output of the pressure generating device and structured to receive and carry the flow of breathing gas generated by the pressure generating device, the method comprising:

generating a first sensed signal comprising a direct measurement of humidity within the airflow path determining based on an output of by a humidity sensor provided in the airflow path a first measurement indicative of an amount of water vapor in the airflow path or an amount of condensation in the airflow path;

generating a number of control signals structured to control an environmental control device structured to control an environmental parameter in an environment outside of the pressure support system, wherein the number of control signals are generated based on at least the first measurement sensed signal and are configured to cause the environmental control device to adjust the environmental parameter in a manner that will reduce a degree or a likelihood of rainout in the airflow path; and transmitting the number of control signals to the environmental control device.

12. The method according to claim 11, wherein the first measurement is a measurement of humidity within the airflow path, and wherein the environmental parameter is ambient temperature within the environment.

13. The method according to claim 12, further comprising generating a first sensed signal indicative of the humidity within the airflow path and a second sensed signal indicative of the ambient temperature within the environment, wherein the first measurement is a humidity measurement based on the first sensed signal, wherein the routines are structured to determine a second measurement indicative of the ambient temperature within the environment based on the second sense signal, and wherein the number of control signals is determined based on the first measurement sensed signal and the second measurement sensed signal.

14. The method according to claim 13, wherein the environmental control device is structured to control the ambient temperature within the environment, and wherein the number of control signals specifies a specific temperature and is structured to control the environmental control device to cause the ambient temperature to equal the specific temperature.

15. The method according to claim 14, wherein the method includes determining a dew point based on the first measurement sensed signal and the second measurement sensed signal, and wherein the specific temperature is based on the dew point.

16. The method according to claim 15, wherein the specific temperature is greater than or equal to the dew point.

17. The method according to claim 15, wherein the specific temperature is offset from the dew point by a predetermined amount.

* * * * *